United States Patent
Wang

(10) Patent No.: US 9,439,867 B1
(45) Date of Patent: Sep. 13, 2016

(54) METHOD FOR MANUFACTURING A COMPOUND DANSHEN DRIPPING PILL

(71) Applicant: TIMING PHARMACEUTICAL CO., LTD., New Taipei (TW)

(72) Inventor: Po-Lun Wang, Taipei (TW)

(73) Assignee: TIMING PHARMACEUTICAL CO., LTD., New Taipei (TW)

( * ) Notice: Subject to any disclaimer, the term of this patent is extended or adjusted under 35 U.S.C. 154(b) by 5 days.

(21) Appl. No.: 14/657,559

(22) Filed: Mar. 13, 2015

(51) Int. Cl.
| | |
|---|---|
| *A61K 36/00* | (2006.01) |
| *A61K 36/537* | (2006.01) |
| *A61K 9/20* | (2006.01) |
| *A61K 36/258* | (2006.01) |
| *A61K 31/047* | (2006.01) |

(52) U.S. Cl.
CPC ............ *A61K 9/2095* (2013.01); *A61K 9/2031* (2013.01); *A61K 31/047* (2013.01); *A61K 36/258* (2013.01); *A61K 36/537* (2013.01)

(58) Field of Classification Search
None
See application file for complete search history.

(56) References Cited

U.S. PATENT DOCUMENTS

2012/0315328 A1  12/2012  Sun et al.

OTHER PUBLICATIONS

Stafford, "Chinese Herbal Medicine Clears US FDA Phase II Trials", HerbalEGram, Oct. 2010, 2 pages, vol. 7, No. 10.

*Primary Examiner* — Qiuwen Mi
(74) *Attorney, Agent, or Firm* — Muncy, Geissler, Olds & Lowe, P.C.

(57) ABSTRACT

A method for manufacturing a compound danshen dripping pill is disclosed. The method comprises: mixing powders of active substances with an excipient in a weight ratio between 1:1 and 1:2 to obtain a mixture; indirectly melting the mixture via a first oil at 75-80° C. until the mixture becomes a molten state; and dripping the melted mixture into a second oil at 3-10° C., cooling and solidifying the melted mixture to obtain the dripping pill. The powders of active substances comprise powders of Chinese *salvia*, powders of *notoginseng* and borneol, while the excipient comprises PEG 1500 and PEG 4000 in a weight ratio between 1:1 and 1:3.

9 Claims, No Drawings

METHOD FOR MANUFACTURING A COMPOUND DANSHEN DRIPPING PILL

BACKGROUND OF THE INVENTION

1. Field of the Invention

The present invention relates to a method and, more particularly, to a method for manufacturing a compound danshen dripping pill. The present invention further relates to the manufactured compound danshen dripping pill.

2. Description of the Related Art

Chinese *salvia* (*Salvia miltiorrhiza*; known as danshen in Chinese) is highly valued for its roots and stems in Chinese medicine. Danshen includes several active ingredients, such as tanshionone, cryptotanshionene and isotanshionone and therefore can be used for coronary atherosclerotic heart disease (CAHD), chest distress, palpitation and menstrual disorder. Specifically, Chinese *salvia* can be used in combination with *notoginseng* (*Panax notoginseng*; known as sanchi or tien-chi *ginseng*) and borneol, forming a compound danshen in the form of powder, solution, tablet or dripping pill.

In a conventional method for manufacturing the compound danshen dripping pill, powders of active substances containing powders of Chinese *salvia*, powders of *notoginseng* and borneol are first mixed with an excipient containing PEG 4000 and PEG 6000 to obtain a mixture. The mixture is then melted in an indirect way using a first oil bath of 85-90° C., followed by dripping into a second oil bath of 6° C. to cool and solidify the melted mixture and obtain the manufactured dripping pill.

However, it is not easy to uniformly mix the powders of active substances with the excipient. When the melted mixture is dripped into the second oil bath via an opening of a dropper, the active substance will easily form a deposit near the opening, choking up the opening and affecting the level of the active substances in the manufactured dripping pill. Moreover, by the conventional method, the manufactured dripping pill shows various diameters and various appearances, not only reducing the desire for the dripping pill but also being difficult to define the dosage of the dripping pill.

In light of this, it is necessary to improve the conventional method for manufacturing the compound danshen dripping pill.

SUMMARY OF THE INVENTION

It is therefore the objective of this invention to provide a method for manufacturing a compound danshen dripping pill with an improved forming rate, thereby obtaining the dripping pill with uniform diameter and uniform level of the active substances.

A method for manufacturing a compound danshen dripping pill includes mixing powders of active substances with an excipient in a weight ratio between 1:1 and 1:2 to obtain a mixture. The powders of active substances comprises powders of Chinese *salvia*, powders of *notoginseng* and borneol, while the excipient comprises PEG 1500 and PEG 4000 in a weight ratio between 1:1 and 1:3. The mixture then is indirectly melted via a first oil at 75-80° C. until the mixture becomes a molten state. Finally, the melted mixture is dripped into a second oil at 3-10° C., cooling and solidifying to obtain the dripping pill.

In a preferred form shown, the powders of active substances, PEG 1500 and PEG 400 are mixed in a weight ratio of 1.75:1:1.

In a preferred form shown, the first oil is set at 78° C., wherein the second oil is set at 6° C.

In a preferred form shown, the powders of active substances comprise 74.26 wt % of the powders of Chinese *salvia*, 24.38 wt % of the powders of *notoginseng* and 1.36 wt % of borneol.

In a preferred form shown, the powders of Chinese *salvia* is obtained by extracting a raw material, concentrating and graining, and the powders of *notoginseng* is also obtained by extracting a raw material, concentrating and graining.

In a preferred form shown, the heated mixture is dripped into the second oil via a dropper set at 70-80° C.

In a preferred form shown, the dropper is set at 75° C.

In a preferred form shown, the dropper has an opening in a diameter of 1.5-3 mm.

A compound danshen dripping pill is manufactured by the method mentioned above.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

DETAILED DESCRIPTION OF THE INVENTION

A method for manufacturing a compound danshen dripping pill according to present invention includes melting a mixture obtained by mixing powders of active substances with an excipient, followed by cooling the melted mixture to obtain the dripping pill.

Specifically, the powders of active substances include powders of Chinese *salvia*, powders of *notoginseng* and borneol. In this embodiment, the powders of active substances include, but not are limited to, 74.26 wt % of the powders of Chinese *salvia*, 24.38 wt % of the powders of *notoginseng* and 1.36 wt % of borneol, which poses an improved effect on promoting blood circulation and removing blood stasis. Moreover, the powders of Chinese *salvia* and the powders of *notoginseng* can be obtained by milling a raw material which is washed and dried. Alternatively, the powders of Chinese *salvia* and the powders of *notoginseng* can be obtained by extracting a raw material, followed by concentrating and graining. In addition, borneol can be synthetic borneol or natural borneol found in cardamon (*Elettaria cardamomum* var. *cardamomum*), ginger (*Zingiber officinale*) and etc. Preferably, the powders of active substances have water content lower than 5%, improving the uniform mixing of the powders of active substances and the excipient. The powders of active substances can be dried to lower water content of the powders of active substances by any conventional means; and in this embodiment, the powders of active substances are dried in an oven set at 80° C. for 12 hours.

The excipient includes PEG 1500 (polyethylene glycols with a molecular weight of 1500) and PEG 4000 (polyethylene glycols with a molecular weight of 4000) in a weight ratio between 1:1 and 1:3. In such performance, the excipient can uniformly mix with the powders of active substances, and form the mixture with a suitable consistency, improving the forming rate of the melted mixture. In this embodiment, the powders of active substances, PEG 1500 and PEG 4000 are mixed in a weight ratio of 1.75:1:1 to obtain the mixture.

The mixture is then melted to molten state. To prevent the melted mixture from spoiling during the melting process, the mixture can be melted in an indirect way. In this embodiment, the mixture is placed in a container made of steel. The container is soaked in an oil bath filling with a first oil heated to achieve 75-80° C. During the melting process, a stir bar set at 500 rpm is adapted to uniformly mix the powders of active substances and the excipient. By using the first oil with a higher specific heat capacity, the mixture can be melted uniformly during the melting process, preventing from the occurrence of bumping. In this embodiment, the first oil is silicone oil (food grade, purchased from Shin-Etsu Chemical Co., Ltd.) with a viscosity at 25° C. of 102 mm$^2$/s, with a specific gravity at 25° C. of 0.996, and with a refractive index at 25° C. of 1.4029.

The melted mixture is subsequently dripped into a shaping tower via a dropper with an opening. A second oil set at 3-10° C. is loaded in the shaping tower, permitting the cooling and the solidification of the melted mixture after the melted mixture is dripped into the second oil at a lower temperature. That is, the dripping pill can be therefore obtained. Shapes or detail structures are not limited. In this embodiment, a tube interconnects the container, and the dropper is mounted at one end of the tube. The shaping tower is placed below the dropper, and therefore the melted mixture can drip into the shaping tower due to the gravity. Moreover, the shaping tower is coupled to a circulation device to draw out the second oil from the bottom of the shaping tower and to introduce the second oil into the top of the shaping tower, permitting the circulation of the second oil. With such performance, the melted mixture can roll in the shaping tower along with the flow of the second oil, and therefore, the dripping pill can be formed in a spherical form. In this embodiment, in order to obtain the dripping pill with a spherical form, the first oil filled in the oil bath is set at 78° C., and the second oil loaded in the shaping tower is set at 6° C. Besides, in this embodiment, the second oil is the silicone oil same as the first oil. The melted mixture is cooled and solidified, but limited to, for 30-40 seconds to obtain the dripping pill.

Moreover, the dropper has a temperature set at 70-80° C., preventing the melted mixture from cooling and solidifying in the tube. The temperature of the dropper can be preferably set at 75° C. to improve the forming rate. Furthermore, the opening has a diameter adjusted according to the weight of the dripping pill. For example, the dripping pill has the weight of 27±2.7 mg while the opening has the diameter of 1.5 mm, the dripping pill has the weight of 32±3.2 mg while the opening has the diameter of 2 mm, and the dripping pill has the weight of 50±5 mg while the opening has the diameter of 3 mm. The shaping tower is coupled to a separating device to separate the dripping pill and the second oil.

Therefore, by forming the mixture with the powders of active substances and the excipient in a weight ratio between 1:1 and 1:2, with the excipient including PEG 1500 and PEG 4000 in a weight ratio between 1:1 and 1:3, and by the uniformly mixed mixture at 75-80° C., the dripping pill manufactured by the method according to the present invention has an equal level of the active substances.

Moreover, by the set temperature of the first oil and the set temperature of the second oil, the dripping pill manufactured by the method according to the present invention forms in spherical form with an equal size.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for manufacturing a compound danshen dripping pill, comprising:
    mixing powders of active substances with an excipient in a weight ratio between 1:1 and 1:2 to obtain a mixture;
    indirectly melting the mixture via a first oil at 75-80° C. until the mixture becomes a molten state; and
    dripping the melted mixture into a second oil at 3-10° C., cooling and solidifying the melted mixture to obtain the dripping pill;
    wherein the powders of active substances comprises powders of Chinese *salvia*, powders of *notoginseng* and borneol;
    wherein the excipient comprises PEG 1500 and PEG 4000 in a weight ratio between 1:1 and 1:3.

2. The method for manufacturing the compound danshen dripping pill as claimed in claim 1, wherein the powders of active substances, PEG 1500 and PEG 400 are mixed in a weight ratio of 1.75:1:1.

3. The method for manufacturing the compound danshen dripping pill as claimed in claim 1, wherein the first oil is set at 78° C., and wherein the second oil is set at 6° C.

4. The method for manufacturing the compound danshen dripping pill as claimed in claim 1, wherein the powders of active substances comprises 74.26 wt % of the powders of Chinese *salvia,* 24.38 wt % of the powders of *notoginseng* and 1.36 wt % of borneol.

5. The method for manufacturing the compound danshen dripping pill as claimed in claim 4, wherein the powders of Chinese *salvia* is obtained by extracting a raw material, concentrating and graining, and wherein the powders of *notoginseng* is obtained by extracting a raw material, concentrating and graining.

6. The method for manufacturing the compound danshen dripping pill as claimed in claim 1, wherein the melted mixture is dripped into the second oil via a dropper set at 70-80° C.

7. The method for manufacturing the compound danshen dripping pill as claimed in claim 6, wherein the dropper is set at 75° C.

8. The method for manufacturing the compound danshen dripping pill as claimed in claim 6, wherein the dropper has an opening in a diameter of 1.5-3 mm.

9. A compound danshen dripping pill, being manufactured by the method as claimed in claim 1.

* * * * *